United States Patent [19]

Berrocal et al.

[11] Patent Number: 5,833,953
[45] Date of Patent: Nov. 10, 1998

[54] FLUORIDATED MICELLAR CASEIN

[75] Inventors: Rafael Berrocal, St-Legier; Jean-Richard Neeser, Savigny; Pierre Tachon, Cugy, all of Switzerland

[73] Assignee: Nestec S.A., Vevey, Switzerland

[21] Appl. No.: 665,120

[22] Filed: Jun. 14, 1996

[30] Foreign Application Priority Data

Jun. 16, 1995 [EP] European Pat. Off. .............. 95201618

[51] Int. Cl.$^6$ .............................. A61K 7/16; A61K 7/18
[52] U.S. Cl. ................................................ 424/49; 424/52
[58] Field of Search ........................................ 424/52, 49

[56] References Cited

FOREIGN PATENT DOCUMENTS

| | | |
|---|---|---|
| 528458 | 2/1993 | European Pat. Off. . |
| 2206049 | 12/1988 | United Kingdom . |
| 9113607 | 9/1991 | WIPO . |
| 9303707 | 3/1993 | WIPO . |
| 9400146 | 1/1994 | WIPO . |

OTHER PUBLICATIONS

Colloids and Surfactants, vol. 3, pp. 177–182, G. Rolla and M. Rykke Evidence For Pressence of Micelle–Like Protein Globules In Human Saliva, p. 178.

Milchwissenschaft, vol. 30, No. 11, 1975 pp. 674–680, A.M. Knoop, K.H. Peters, "Phoaphataseaktivitat in Sauermilch"—pp. 675–676.

*Primary Examiner*—John Kight
*Assistant Examiner*—D. Margaret M. Mach
*Attorney, Agent, or Firm*—Pennie & Edmonds LLP

[57] ABSTRACT

Process for the preparation of fluoridated casein micelles, in which at least 100 ppm of a soluble fluoride salt are added of a solution comprising micellar casein and the fluoridated micellar casein is isolated. Food or pharmaceutical composition for treating dental caries or plaque comprising an effective quantity of fluoridated micellar casein or its micellar subunits.

19 Claims, No Drawings

FLUORIDATED MICELLAR CASEIN

TECHNICAL FIELD

The subject of the present invention is the fluoridation of the casein of a milk and the use of the fluoridated caseins as agents for treating dental pathologies.

BACKGROUND

Cow's milks comprising fluorine salts, such as sodium fluoride, has already been proposed for reducing the incidence of dental caries in human health (Beddows G. et al., Analyst, 106, 1341–1344, 1981).

Other studies have, moreover, shown that most of the fluoride exists in equilibrium in a cow's milk in a free ionic form, while a small part may be complexed by the milk calcium. The fluoride is not therefore necessarily complexed with the milk proteins, especially with the micellar casein (Beddows G. et al., J. Fd Technology, 17, 55–62, 1982).

Moreover, it is known that, in a micellar casein solution, an excess of fluoride salts is capable of dividing the micellar casein into its micellar subunits through the action of the extra ionic strength provided by the fluoride (Carroll et al., J. Dairy Science, 54, 752, 1971).

Finally, EP604802 shows that micellar casein has an anti-dental caries activity and EP283675 shows that the kappa-caseinoglycopeptides exposed at the surface of casein micelles also have an anti-dental caries and plaque activity.

SUMMARY OF THE INVENTION

The object of the present invention is to provide new micellar casein derivatives which can be used for oral hygiene in man or in animals.

To this end, in the process for the preparation of fluoridated casein micelles according to the present invention, at least 100 ppm of a soluble fluoride salt is added to a solution comprising casein micelles and the fluoridated micellar casein is isolated.

The invention also relates to the fluoridated casein micelles and to the food or pharmaceutical compositions for treating dental or dentinal pathologies comprising an effective quantity of fluoridated micellar casein or of its micellar subunits.

Finally, the present invention also relates to the use of fluoridated micellar casein or of its fluoridated micellar subunits for the preparation of a composition for treating dental or dentinal pathologies.

The invention has made it possible, surprisingly, to manufacture for the first time fluoridated micellar casein whose micellar structure is preserved.

The fluoride may therefore combine with the micelle without, however, disrupting its structure or destroying it. The invention therefore contradicts acknowledged scientific knowledge which shows that fluoride, depending on its concentration, tends either to destroy the micelle or practically not to form a complex with milk proteins, and in particular milk micellar casein (Beddows G. et al., J. Fd Technology, 17, 55–62, 1982).

The fluoridated micellar casein according to the invention is furthermore complexed with a large quantity of fluoride. It has indeed been possible to observe that more than 20%, or even 50%, of the initial free fluoride is thus complexed with the casein, allowing their use to be envisaged for human or animal oral hygiene as anti-dental plaque, anti-dental caries, anti-periodontopathy and anti-dentinal hyperaesthesia agent.

DETAILED DESCRIPTION OF THE INVENTION

To carry out the present invention, there may be used as solution comprising micellar casein a milk obtained from an animal such as a cow, a goat or a ewe, for example, or a fraction of the milk comprising micellar casein. However, it is advisable to ensure that the important compounds for maintaining the micellar structure, such as citrate, for example, are present in the fraction in sufficient quantities. It should, however, be noted that these compounds are isolated from the same fraction as that which comprises the micellar casein when an animal milk is microfiltered, ultrafiltered or diafiltered, and the retentate is isolated.

At least 100 ppm of a water-soluble fluoride salt is then added to the solution. The soluble fluoride salt may be chosen from sodium fluoride and sodium fluorophosphates, for example. Preferably, the fluoride salt is mixed with the solution for about 1 min to 5 h at a temperature of between after 5° and 70° C. so as to promote the complexing of the fluoride with the micellar casein. To prepare fluoridated caseins whose micellar structure is preserved, about 100 to 2000 ppm of a soluble fluoride salt may be added to the solution. On the other hand, if it is desired to prepare micellar subunits of fluoridated caseins, more than 2000 ppm of a soluble fluoride salt may be added to the solution.

Finally, if an animal milk has been supplemented with a fluoride salt, the micellar or submicellar fluoridated casein may be isolated by microfiltration, ultrafiltration and/or diafiltration of the milk. Preferably, this milk is microfiltered on a mineral membrane having a porosity of about 0.1–0.2 $\mu$m. On the other hand, if an animal milk fraction has been supplemented with a fluoride salt, it is possible not to try to further purify the fluoridated casein since its concentration is sufficiently high.

However, it is advantageous to obtain a powder comprising mainly fluoridated casein (whose fluorine is complexed with the micelles or with the micellar subunits), by drying the fraction in which the fluoridated casein has been isolated, for example by spray-drying.

The fluoridated micellar casein according to the present invention has a micellar spatial structure which is identical to that of the original milk micellar casein. The interactions between the micelle and the fluoride appear to be stable ionic interactions; however, other types of interactions are not excluded (physical absorption, covalent bonding, for example).

The micellar casein subunits complexed to fluorine also have an advantageous structure. These subunits are formed of aggregated caseins which are complexed with fluoride molecules. These fluoridated micellar subunits also potentially have a remarkable anti-dental caries and plaque activity because they comprise kappa-caseinoglycopeptides, caseinophosphopeptides and fluoride which are known to have an anti-dental caries and plaque activity.

The fluoridated micellar casein or its micellar subunits can have at least about 5 mg fluoride per 100 g casein or subunit. Advantageously, about 50 to 5000 mg can be used, with between about 100 and 2,000 mg being preferred. The fluoride can be associated with the micellar structure in a number of ways as explained above.

The present invention therefore also relates to the use of fluoridated micellar casein or of its micellar subunits for the preparation of a composition for treating dental caries or plaque. The fluoridated micellar casein and its subunits can thus be used in a method for the prophylactic and/or therapeutic treatment of dental plaque, dental caries and periodontopathies and dentinal hyperaesthesias.

For that, an acceptable food or pharmaceutical composition is prepared, comprising an effective quantity of fluoridated micellar casein or of its micellar subunits, optionally in combination with a pharmaceutically acceptable carrier and it is administered orally to man or to an animal. Any acceptable pharmaceutical carrier can be used, and these are generally known to those of ordinary skill in the art. The examples illustrate preferred carriers and compositions.

Such compositions can be prepared by adding to a food or pharmaceutical composition, during their preparation, at least about 0.1% of the fluoridated casein according to the present invention, for example. It is also possible to envisage adding directly, to a food or pharmaceutical composition having a liquid or at least pasty consistency, at least about 0.1% of a mixture comprising a micellar casein powder and at least 100 ppm of a soluble fluoride salt. The fluoridated caseins according to the present invention can therefore also be manufactured during the manufacture of a food or pharmaceutical product.

The compositions according to the invention are thus food or pharmaceutical compositions comprising an effective quantity of fluoridated micellar casein or micellar subunits, that is to say a sufficient quantity, generally of 0.1 to 90% by weight, but preferably 1 to 20%, to inhibit the adhesion of dental plaque and caries bacteria, for example bacteria of the genus *Actinomyces naeslundii*, *Actinomyces viscosus*, *Streptococcus sanguis*, *Streptococcus mutans* and/or *Streptococcus sobrinus*.

The composition according to the invention may comprise, in addition, conventional ingredients, well known to persons skilled in the art, which depend on the form and the use of the final product. For a predominantly food use, the composition may be a confectionary item, a sweetened drink or a milk capable of being fermented, for example. For a predominantly pharmaceutical application, the composition may be in the form of a dental cream, a dental paste, a dental chewing gum or a mouthwash, for example.

In the case of a dental cream or paste, the composition may comprise, in addition, a humectant liquid phase, a binder or a thickener, abrasive particles, a surfactant and flavourings. The composition may thus comprise about 10 to 85% of a humectant liquid phase such as a glycerol, sorbitol, propylene glycol or lactitol syrup, about 0.1 to 10% of a binder or a thickener such as sodium carboxymethylcellulose, xanthan gums or silica gels, about 0.5 to 5% of a surfactant which does not associate the micelle or the micellar subunits, and at least about 3% of abrasive agents such as silicas, calcium carbonates, anhydrous dicalcium phosphate or hydroxyapatite, for example.

The composition according to the invention may also comprise other optional ingredients; for example anti-plaque and/or antimicrobial agents such as chlorhexidine, 2,4,4'-trichloro-2'-hydroxydiphenyl ether, zinc compounds, alkali metal pyrophosphates, sodium fluoride or sodium fluorophosphate; sweeteners such as saccharine; opacifying agents such as titanium dioxide; coloring agents; buffering agents which maintain an appropriate pH, such as benzoic acid or its salt. Preferably, a buffer having a pH greater than 5 is chosen so as to avoid dissociation of the micelle.

EXAMPLES

The examples below are presented by way of illustration of the process, of the composition and of the use according to the present invention. In these examples, the parts and percentages are given by weight, unless otherwise indicated.

Example 1

A micellar-casein solution is prepared by microfiltering a cow's milk on a mineral membrane having a porosity of about 0.2 μm and it then is spray-dried.

To determine the distribution of fluorine in a micellar casein suspension, an aqueous solution is prepared comprising 20% by weight of micellar casein. It should be noted that this suspension comprises, moreover, 200 ppm of free calcium.

58.25 mg of sodium fluoride are added to 100 g of the micellar solution (that is to say 600 ppm), the solution is stirred for one hour and then it is ultracentrifuged at 100,000 g for 90 min. The centrifugation pellets are then rinsed with distilled water, dispersed in water and then freeze-dried. The quantity of fluorine remaining in the micelle is then measured by the method of Beddows G. et al., (Analyst, 106, 1341–1344, 1981).

The results presented in the table in Example 2 show that 59.13% of the fluorine added in the form of sodium fluoride is found together with the micelle during the ultracentrifugation. Furthermore, the color and the consistency of the centrifugation pellet are characteristic of the presence of micelles. The micellar structure may be confirmed by electron microscopy. Given that the sodium fluoride does not precipitate naturally at 100,000 g, the results therefore tend to show that the fluoride binds to the micelle by a mechanism which may involve physical absorption, ion exchange and/or covalent bonding, for example.

These results contradict the general technical teaching which shows that more than 80% of the fluoride, or even 95%, remains in solution after ultracentrifugation of a fluoridated milk and that the complexing of the fluorine with the milk proteins is inhibited by free calcium contents greater than 10 ppm (Beddows G. et al., J. Fd Technology, 17, 55–62, 1982).

Example 2

30 mg of sodium fluorophosphate are added to 100 g of the micellar solution of Example 1 (that is to say 300 ppm), the solution is stirred for one hour and then it is ultracentrifuged at 100,000 g for 90 min. The centrifugation pellets are then rinsed with distilled water, dispersed in water and then freeze-dried. The quantity of fluorine remaining in the micelle is then measured by the method mentioned in Example 1.

The table below illustrates the experimental results of Examples 1 and 2.

| Examples | 1)Micelle + NaF | 2)Micelle + NaF6F |
|---|---|---|
| Weight of the initial solution in g of liquid | 100 | 100 |
| Weight of initial micelle in g of powder | 10.108 | 10.097 |
| Fluoride added in mg/100 g of liquid | 26.47 | 20.36 |
| Ultracentrifuged micelle as powder | 6.66 | 7.12 |
| Fluoride analysed in mg/100 g of micelle as powder | 235 | 112 |
| Fluoride calculated in mg/100 g of liquid | 15.65 | 7.97 |
| [Fluoride calculated/Fluoride added] % | 59.13 | 39.17 |

The results show that 39.13% of the fluoride added in the form of sodium fluorophosphate is found together with the micelle when the fluoridated solution is ultracentrifuged. Furthermore, the color and the consistency of the centrifugation pellet are also characteristic of the presence of micelles. The micellar structure is confirmed by electron microscopy. Given that the sodium fluorophosphate does not precipitate naturally at 100,000 g, the results therefore tend to show that the fluoride binds to the micelle by a mechanism which may involve physical absorption, ion exchange and/or covalent bonding, for example.

Example 3

A fluoridated micellar casein powder is prepared by the method described in Examples 1 and 2, except that 1000 ppm of sodium fluoride are added to the micellar solution.

Example 4

A fluoridated micellar casein powder is prepared by adding to a pasteurized cow's milk 1000 ppm of sodium fluorophosphate, homogenizing the milk at room temperature for 10 min, ultrafiltering the milk on a membrane of porosity 0.2 $\mu$m and then spray-drying the retentate.

Example 5

To prepare a fluoridated micellar casein subunit powder, a pasteurized cow's milk is microfiltered on a mineral membrane having a porosity of about 0.2 $\mu$m, then the retentate is diluted with water so as to obtain a solution comprising 20% by weight of micellar casein. 3000 ppm of sodium fluoride are added to the micellar casein solution, the solution is homogenized for a few minutes, and then spray-dried. The powder thus obtained can be advantageously used for the preparation of food or pharmaceutical compositions for treating dental pathologies.

To confirm the presence of fluoridated micellar subunits, a solution is prepared comprising 20% of fluoridated micellar subunit powder, and then centrifuged at 100,000 g. The color and the consistency of the centrifugation pellet are characteristic of the dissociation of micelles into their subunits. This subparticulate structure can be confirmed by electron microscopy. Moreover, the centrifugation pellets can be rinsed with distilled water, dispersed in water, freeze-dried, and their fluorine content assayed. The results show that the powder thus obtained is particularly high in fluorine.

Example 6

A dental paste for removing dental calculus and for the prophylaxis of dental caries is prepared. This powder comprises 5% calcium carbonate, 10% silica aerogel (Gasil 23), 40% sorbitol syrup, 1% sodium carboxymethylcellulose, 6.5% of a fluoridated casein micelle powder obtained in Example 4, 0.2% sodium saccharinate, 1% titanium dioxide, 0.04% Formalin, 1% flavouring and the remainder is water.

Example 7

The same dental paste as that described in Example 5 is prepared, except that the 5% of a fluoridated casein micelle powder is replaced with 5% of a casein micelle subunit powder obtained in Example 5.

Example 8

A mouthwash for the prophylaxis of dental caries and the treatment of periodontopathies and dentinal hyperaesthesia is prepared. This wash comprises 10% fluoridated casein micelle powder obtained in Example 4, 0.1% benzoic acid, 0.2% sodium saccharinate, 0.1% quinoline yellow, 0.1% patent blue, 3% ethyl alcohol at 95%, and the remainder is water.

What is claimed is:

1. Fluoridated micellar casein.

2. Fluoridated micellar casein produced by a process which comprises:

adding at least 100 ppm of a soluble fluoride salt to a solution which contains water-insoluble micellar casein to form water-insoluble fluoridated micellar casein; and subsequently isolating the water-insoluble fluoridated micellar casein that is produced.

3. Casein according to claim 2 wherein the fluoride salt is sodium fluoride or a sodium fluorophosphate.

4. Casein according to claim 1 containing at least 5 mg fluoride per 100 g micelle.

5. Casein according to claim 2 containing at least 5 mg fluoride per 100 g micelle.

6. Casein according to claim 1 containing between about 50 and 5,000 mg fluoride per 100 g micelle.

7. Casein according to claim 2 containing between about 50 and 5,000 mg fluoride per 100 g micelle.

8. A method for treating dental carries or plaque which comprises applying an effective amount of a composition of a water-insoluble fluoridated micellar casein or its fluoridated micellar subunits to teeth.

9. The method of claim 8 wherein the composition contains at least about 0.1% of the fluoridated casein or subunit and is in the form of a dental cream, paste, chewing gum or mouthwash.

10. The method of claim 8 wherein the fluoridated micellar casein or subunit contains at least about 5 mg fluoride per 100 g micelle or subunit.

11. A method for treating dental carries or plaque which comprises applying an effective amount of the casein of claim 1 to teeth.

12. A method for treating dental carries or plaque which comprises applying an effective amount of the casein of claim 2 to teeth.

13. A method for treating dental carries or plaque which comprises applying an effective amount of the casein of claim 4 to teeth.

14. A method for treating dental carries or plaque which comprises applying an effective amount of the casein of claim 6 to teeth.

15. A food or pharmaceutical composition comprising a water-insoluble fluoridated micellar casein or its fluoridated micellar subunits and a pharmaceutically acceptable carrier.

16. The composition of claim 15 wherein the composition contains at least about 0.1% of the fluoridated casein or subunit and is in the form of a dental cream, paste, chewing gum or mouthwash.

17. The method of claim 8 wherein the composition contains at least about 0.1% of the fluoridated casein or subunit and is in the form of a confectionery item, a sweetened drink or a milk.

18. Fluoridated micellar casein produced by a process which comprises:

adding about 100–2000 ppm of a soluble fluoride salt to a milk which contains at least about 10% by weight of insoluble micellar casein to form a water-insoluble fluoridated micellar casein; and subsequently isolating the water-insoluble fluoridated micellar casein that is produced.

19. Fluoridated micellar casein produced by a process which comprises:

adding about 2000–3000 ppm of a soluble fluoride salt to a milk which contains at least about 10% by weight of water-insoluble micellar casein to form a water-insoluble fluoridated micellar casein; and subsequently isolating the water-insoluble fluoridated micellar casein that is produced.

* * * * *